(12) United States Patent
Heuscher

(10) Patent No.: US 7,305,063 B2
(45) Date of Patent: Dec. 4, 2007

(54) CYLINDRICAL X-RAY TUBE FOR COMPUTED TOMOGRAPHY IMAGING

(75) Inventor: Dominic J. Heuscher, Aurora, OH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 31 days.

(21) Appl. No.: 10/564,573

(22) PCT Filed: Jul. 15, 2004

(86) PCT No.: PCT/IB2004/002324

§ 371 (c)(1),
(2), (4) Date: Jan. 13, 2006

(87) PCT Pub. No.: WO2005/008716

PCT Pub. Date: Jan. 27, 2005

(65) Prior Publication Data

US 2006/0182223 A1    Aug. 17, 2006

Related U.S. Application Data

(60) Provisional application No. 60/488,675, filed on Jul. 18, 2003.

(51) Int. Cl.
*G01N 23/00* (2006.01)
(52) U.S. Cl. .......................... 378/12; 378/125; 378/137; 378/147; 378/151
(58) Field of Classification Search ................ 378/119, 378/121–140, 143, 144, 147–149, 11, 12; 250/363.1, 505.1
See application file for complete search history.

(56) References Cited

U.S. PATENT DOCUMENTS

| 3,836,805 | A |   | 9/1974 | Kok ............................. 313/60 |
| 4,002,917 | A | * | 1/1977 | Mayo .......................... 378/14 |
| 4,039,836 | A | * | 8/1977 | Shaw, IV ..................... 378/91 |
| 4,162,420 | A |   | 7/1979 | Grady ......................... 313/60 |
| 4,250,425 | A |   | 2/1981 | Gabbay et al. ............... 313/60 |

(Continued)

FOREIGN PATENT DOCUMENTS

WO    WO 2004/037088 A1    5/2004

OTHER PUBLICATIONS

SEERAM; Computed Tomography-Physical Principles Clinical Applications & Quality Control; 1994; W.B. Saunders Co.; pp. 102, 103, 184, 185.

*Primary Examiner*—Jurie Yun

(57) ABSTRACT

A computed tomography imaging system includes an x ray tube (12, 212) that injects an x ray conebeam into an examination region (14). The x ray tube (12, 212) includes a rotating cylindrical anode (30, 230, 330, 430) having a target outer surface region. The cylindrical anode (30, 230, 330, 430) rotates about a longitudinally aligned cylinder axis (32). Electrons are accelerated toward a selected spot on the target outer surface region of the cylindrical anode (30, 230, 330, 430). Electrostatic or electromagnetic deflectors (64, 68) sweep the selected spot back and forth across the target outer surface region of the cylindrical anode (30, 330, 430). The imaging system further includes a rotating gantry (22) that revolves the x ray tube (12, 212) about the examination region (14) around a rotation axis that is parallel to the cylindrical axis, and an x-ray detector (16) arranged to detect x rays after said x rays pass through the examination region (14).

27 Claims, 9 Drawing Sheets

U.S. PATENT DOCUMENTS

| | | | |
|---|---|---|---|
| 4,523,327 A | 6/1985 | Eversole | 378/124 |
| 5,313,510 A | 5/1994 | Ebersberger et al. | 378/12 |
| 5,625,661 A | 4/1997 | Oikawa | 378/15 |
| 6,125,167 A | 9/2000 | Morgan | 378/124 |
| 6,229,870 B1 | 5/2001 | Morgan | 378/9 |
| 6,583,420 B1 * | 6/2003 | Nelson et al. | 250/397 |
| 2004/0081270 A1 | 4/2004 | Heuscher | 378/4 |

* cited by examiner

CYLINDRICAL X-RAY TUBE FOR COMPUTED TOMOGRAPHY IMAGING

CROSS REFERENCE TO RELATED APPLICATIONS

This application claims the benefit of U.S. provisional application Ser. No. 60/488,675 filed Jul. 18, 2003, which is incorporated herein by reference.

The following relates to the radiation generation arts. It finds particular application in x-ray computed tomography imaging, and will be described with particular reference thereto. However, it also finds application in other arts that employ x-ray tubes or other radiation sources.

In transmission computed tomography, an x-ray tube mounted on a rotating gantry injects an x-ray beam into an examination region defined by the rotating gantry. After passing through the examination region and being partially absorbed with an imaging subject disposed therein, the absorption-attenuated x-ray beam is measured by an x-ray detector array. The rotating gantry rotates to acquire angular views of the imaging subject angularly spanning about 180° or more. In helical scanning, the rotating gantry rotates continuously as the subject is moved or reciprocated longitudinally. An image reconstruction processor employs filtered backprojection or another reconstruction technique to produce a reconstructed volume image based on the acquired x-ray measurements of the slab defined by the longitudinal reciprocation, typically 2-20 cm.

Characteristics of the x-ray tube can limit the performance of the computed tomography imaging scanner in various ways. Gantry rotation speed is limited by x-ray intensity. The rotation should be slow enough to provide adequate time-integrated signal intensity over each angular viewing interval. Hence, higher x-ray output intensity can translate to faster gantry rotation rates and improved spatial and temporal resolution.

The x-ray intensity generated by an x-ray tube is typically thermally limited. A peak temperature is reached at a spot where accelerating electrons strike the anode surface. The x-ray tube anode is generally disk-shaped and rotated to distribute heating across a target track near an outer diameter of the anode disk. Anode thermal characteristics are suitably quantified in terms of a peak temperature at the x-ray generation spot (this spot moves around the target track as the anode rotates) and a base temperature corresponding to an elevated temperature of the anode as a whole due to thermal dissipation into the anode. Anode rotation and other thermal design techniques provide some control of anode heating; however, anode heating still commonly constrains the x-ray output intensity.

In conebeam computed tomography, the cone angle is also generally limited by the x-ray tube. The target track along which the x-ray generation spot travels is beveled or otherwise arranged at a shallow anode target angle respective to the incident electron beam. The anode target angle is about 7°-10° in present x-ray tubes. Shallower angles are impractical due to the heel effect. The target angle limitation, in turn, imposes a limit on the maximum cone angle. This cone angle limitation is particularly problematic in cone beam computed tomography scanners for which a larger cone angle enables greater coverage and faster volumetric imaging.

Resolution uniformity is also limited by the x-ray tube. The heel effect limits the anode target angle to about 7°-10°, which in turn introduces substantial resolution anisotropy due to an elongated electron beam footprint on the disk anode.

The present invention contemplates an improved apparatus and method that overcomes the aforementioned limitations and others.

According to one aspect, a computed tomography imaging system includes an x-ray tube that injects an x-ray conebeam into an examination region. The x-ray tube includes a rotating cylindrical anode having a target outer surface region. The cylindrical anode rotates about a longitudinally aligned cylinder axis. An electron accelerating means accelerates electrons toward at least one selected spot on the target outer surface region of the cylindrical anode. A sweep means relatively longitudinally sweeps the at least one selected spot across the target outer surface region of the cylindrical anode. The imaging system further includes a revolving means for revolving the x-ray tube about the examination region, and an x-ray detector arranged to detect x-rays after said x-rays pass through the examination region.

According to another aspect, a computed tomography imaging method is provided. An x-ray tube is revolved about an examination region. The x-ray tube is operated to inject an x-ray beam into the examination region, The operating of the x-ray tube includes: rotating a cylindrical anode about a cylinder axis, the cylindrical anode having a target outer surface region; accelerating electrons toward at least one selected spot on the target outer surface region of the cylindrical anode; and relatively sweeping the at least one selected spot across the target outer surface region of the cylindrical anode along a beam trajectory substantially parallel to the cylinder axis. X-rays are detected after said x-rays pass through the examination region.

One advantage resides in providing a larger cone angle that is not limited by the heel effect.

Another advantage resides in providing improved image resolution uniformity.

Yet another advantage resides in improved thermal characteristics of an x-ray tube by distributing heating across a cylindrical anode.

Still yet another advantage resides in obtaining an axial scanning component by sweeping the x-ray beam or beams rather than by moving a subject support couch.

Numerous additional advantages and benefits will become apparent to those of ordinary skill in the art upon reading the following detailed description of the preferred embodiments.

The invention may take form in various components and arrangements of components, and in various process operations and arrangements of process operations. The drawings are only for the purpose of illustrating preferred embodiments and are not to be construed as limiting the invention.

FIG. 1 diagrammatically shows a computed tomography imaging system that incorporates an x-ray tube that includes a cylindrical anode.

FIG. 2 shows a first embodiment of the x-ray tube, in which an electron beam longitudinally sweeps across an outer surface of the cylindrical anode.

FIG. 3 diagrammatically shows electron beam and conebeam parameters for defining a fan angle α of the conebeam.

FIG. 4 diagrammatically shows length and width dimensions of the electron beam footprint on the cylindrical anode.

Figure 9:
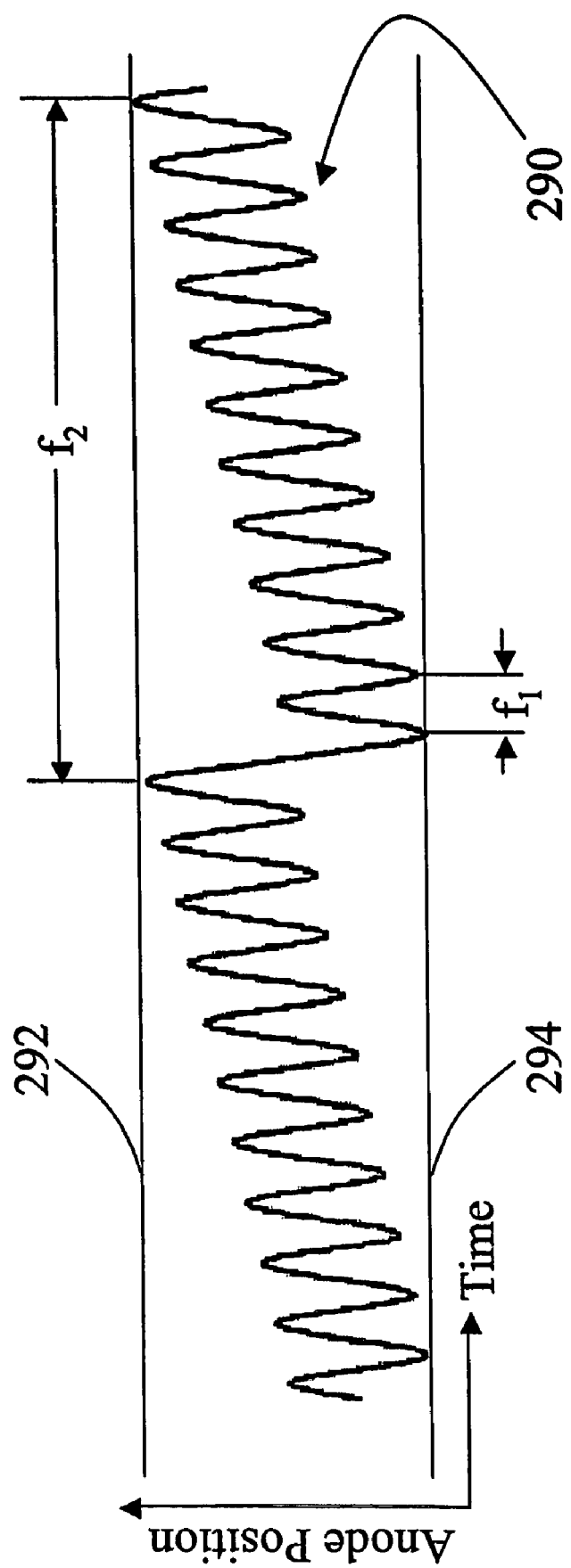

FIG. 9 plots a preferred reciprocating anode trajectory.

Figure 10:
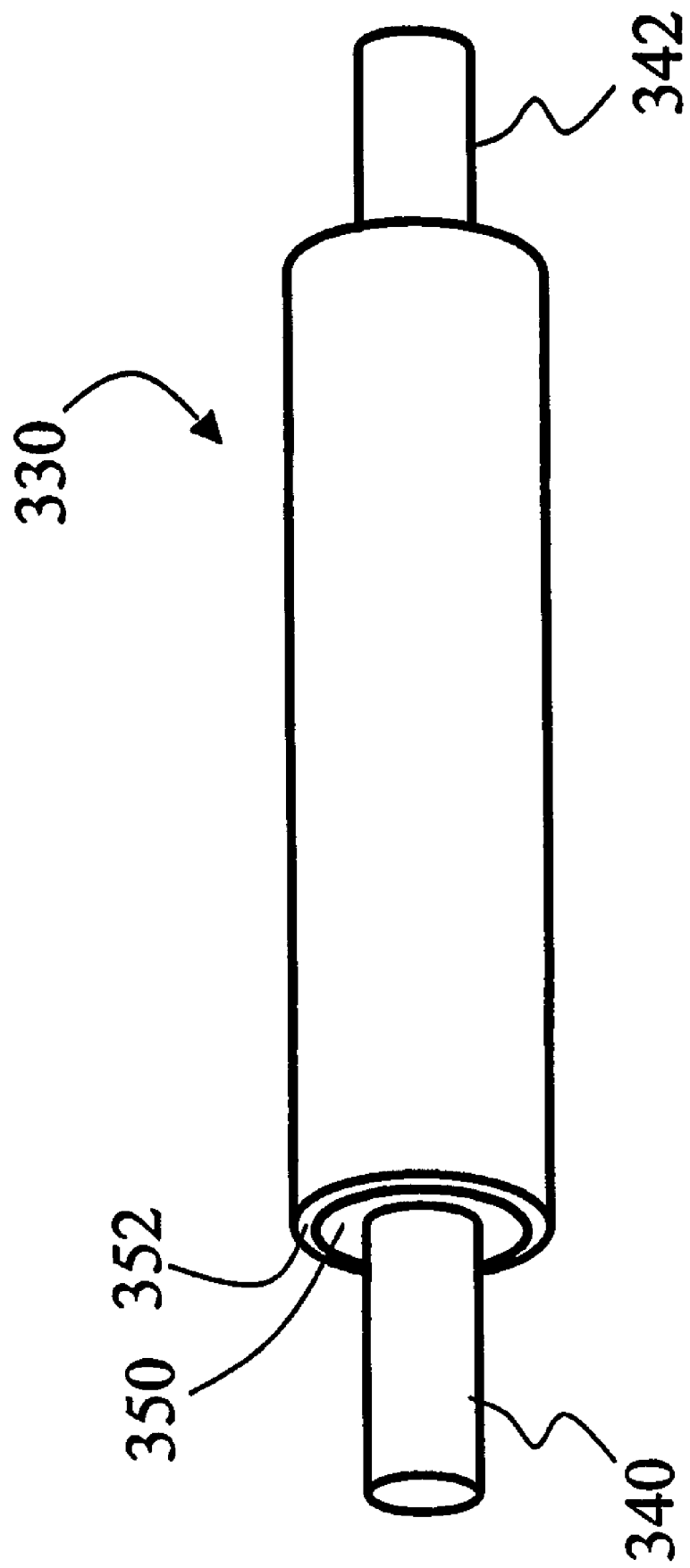

FIG. 10 shows an alternative cylindrical anode having a lightweight central supporting cylinder and a high x-ray yield metallic coating.

Figure 11:
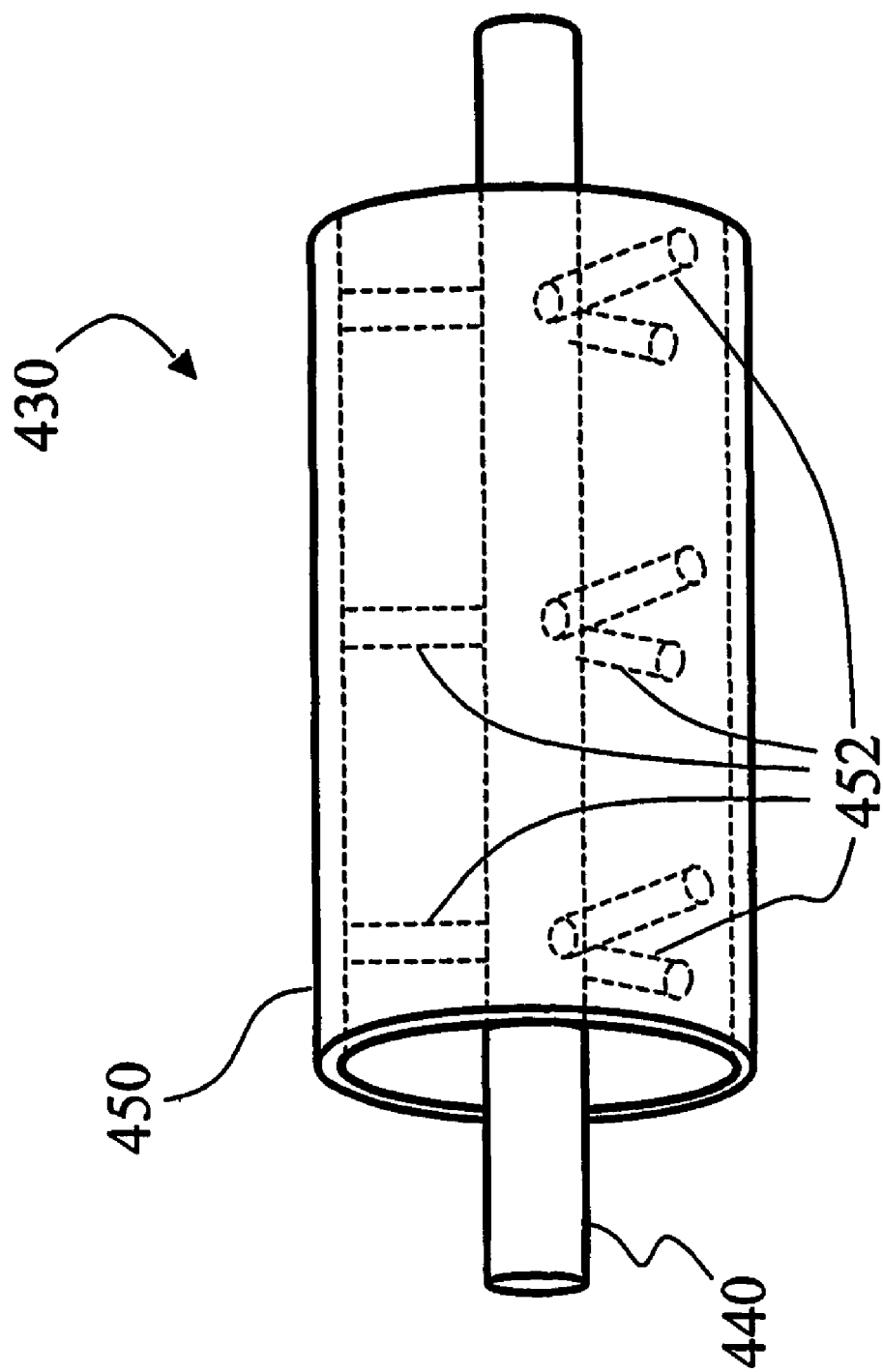

FIG. 11 shows another alternative cylindrical anode having an outer hollow cylindrical shell secured to a unitary shaft by structural support members.

Figure 1:
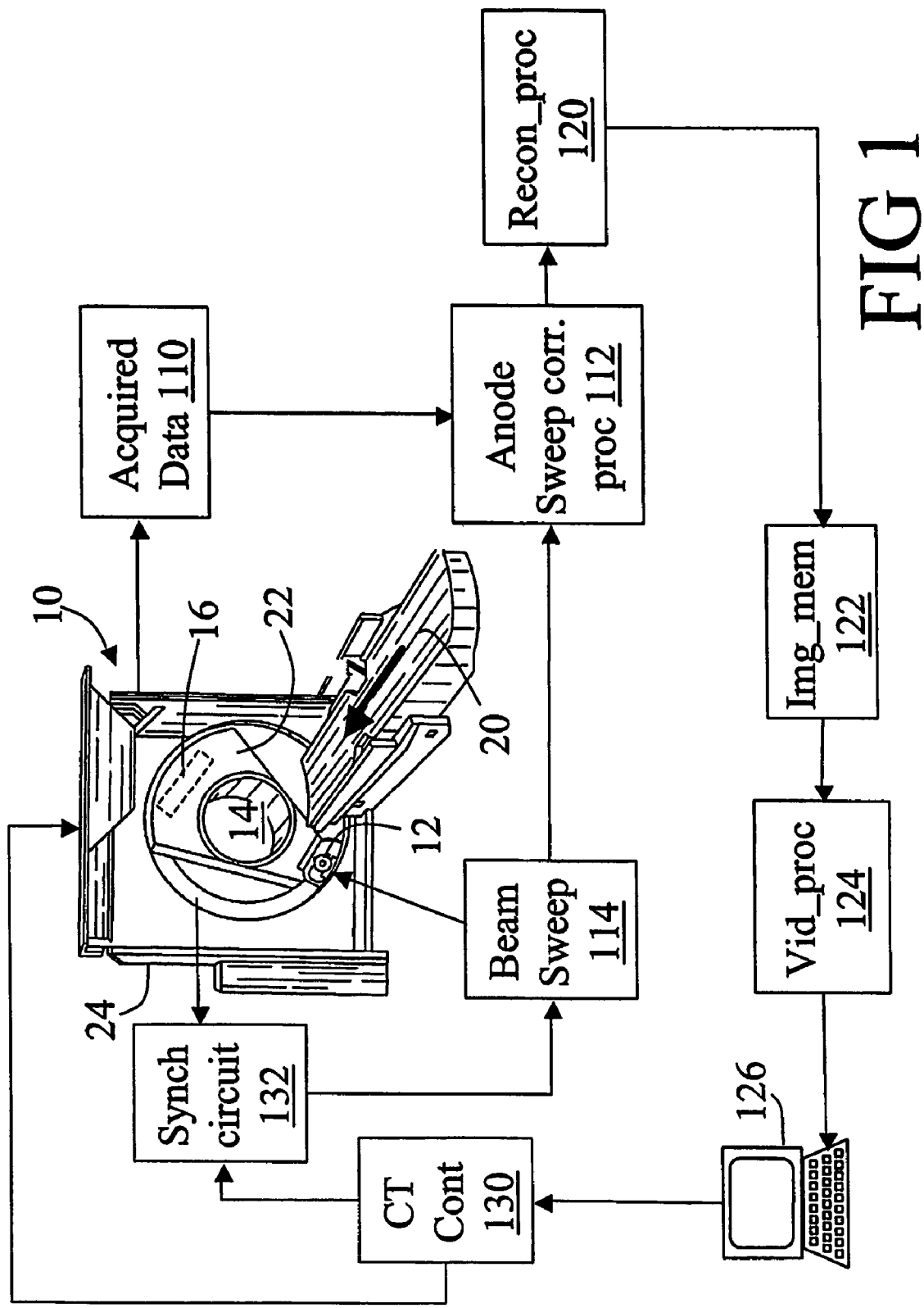

With reference to FIG. 1, a computed tomography imaging system includes a computed tomography imaging scanner 10 having an x-ray tube 12 that injects an x-ray conebeam into an examination region 14. An imaging subject arranged in the examination region 14 absorbs a portion of the x-ray intensity, and the absorption-attenuated x-rays are detected by an x-ray detector 16 after passing through the examination region 14. Preferably, the x-ray detector 16 includes a two-dimensional grid or array of detector elements that substantially spans a cross-sectional area of the x-ray conebeam at the detector.

A subject couch or other subject support 20 is linearly movable in a z-direction as indicated in FIG. 1. The subject support 20 is linearly movable to optionally move the subject linearly in the examination region 14. A rotating gantry 22 rotates to effect revolving of the x-ray tube 12 and the x-ray detector 16 around the examination region 14. The x-ray tube 12 revolves around an axis of revolution corresponding to or parallel to the z-axis. The x-ray tube 12 and the x-ray detector 16 are oppositely arranged on the rotating gantry 22 to ensure that the detector 16 remains in position to detect x-rays generated by the x-ray tube 12. Although the detector 16 is shown in FIG. 1 as mounted on the rotating gantry 22, it is also contemplated to employ a stationary detector band disposed on a stationary gantry 24.

Figure 2:
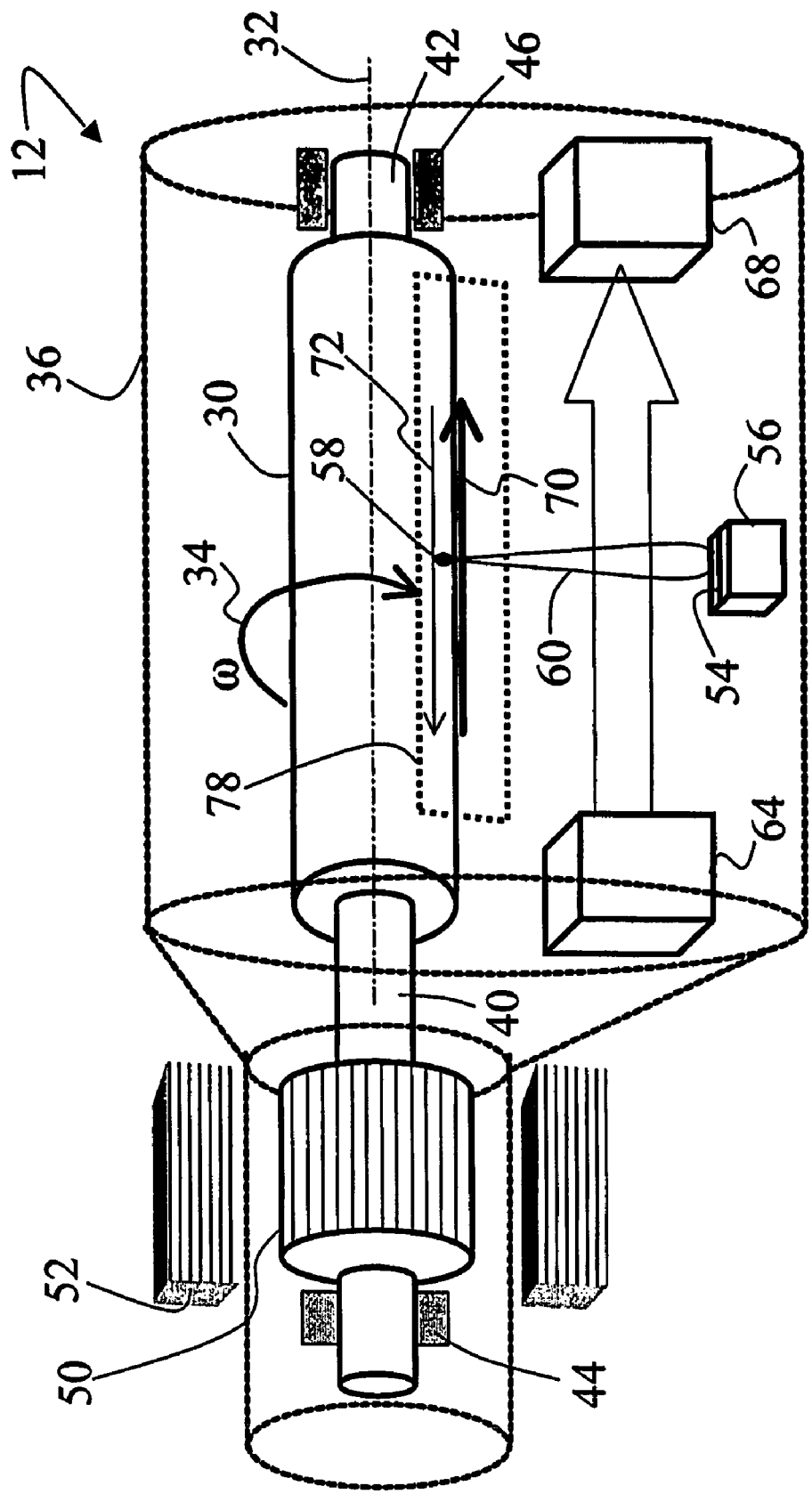

With continuing reference to FIG. 1 and with further reference to FIG. 2, the x-ray tube 12 includes a cylindrical anode 30 defining a longitudinal cylinder axis 32 that is preferably parallel to the z-direction of FIG. 1, so that the cylinder axis 32 is parallel to the axis of rotation of the rotating gantry 22. The cylindrical anode 30 rotates about the cylinder axis 32 as indicated by a curved rotation arrow 34. The cylindrical anode 30 is rotatably secured within an evacuated frame 36 (shown in phantom) by a drive shaft 40 and an end shaft 42, which in turn are supported by oil-free bearing assemblies 44, 46 that are secured to the evacuated frame 36. Motor rotor windings 50 disposed on the drive shaft 40 cooperate with stationary motor stator windings 52 (shown by sectional portion) disposed outside of the evacuated frame 36 to effect rotation of the cylindrical anode 30.

An electron source 54, such as a heated filament or film, disposed in a cathode cup 56 generates electrons. The cathode cup 56 is shaped and electrically biased relative to the cylindrical anode 30 to accelerate and focus the generated electrons toward a selected focal spot 58 on a target outer surface region of the cylindrical anode 30. The accelerated electrons are focused to define an electron beam 60. An electron deflector including biased electrodes 64, 68 electrostatically or electromagnetically deflect the electron beam 60 to sweep the selected spot 58 along a longitudinal sweep trajectory indicated by thick arrow 70. At the end of the sweep 70 a fast retrace indicated by thin arrow 72 returns the selected spot 58 to the initial point of the sweep trajectory 70 to complete a sweep cycle. Alternatively, the selected spot 58 can be swept back in the opposite direction in a reciprocating fashion.

Figure 3:
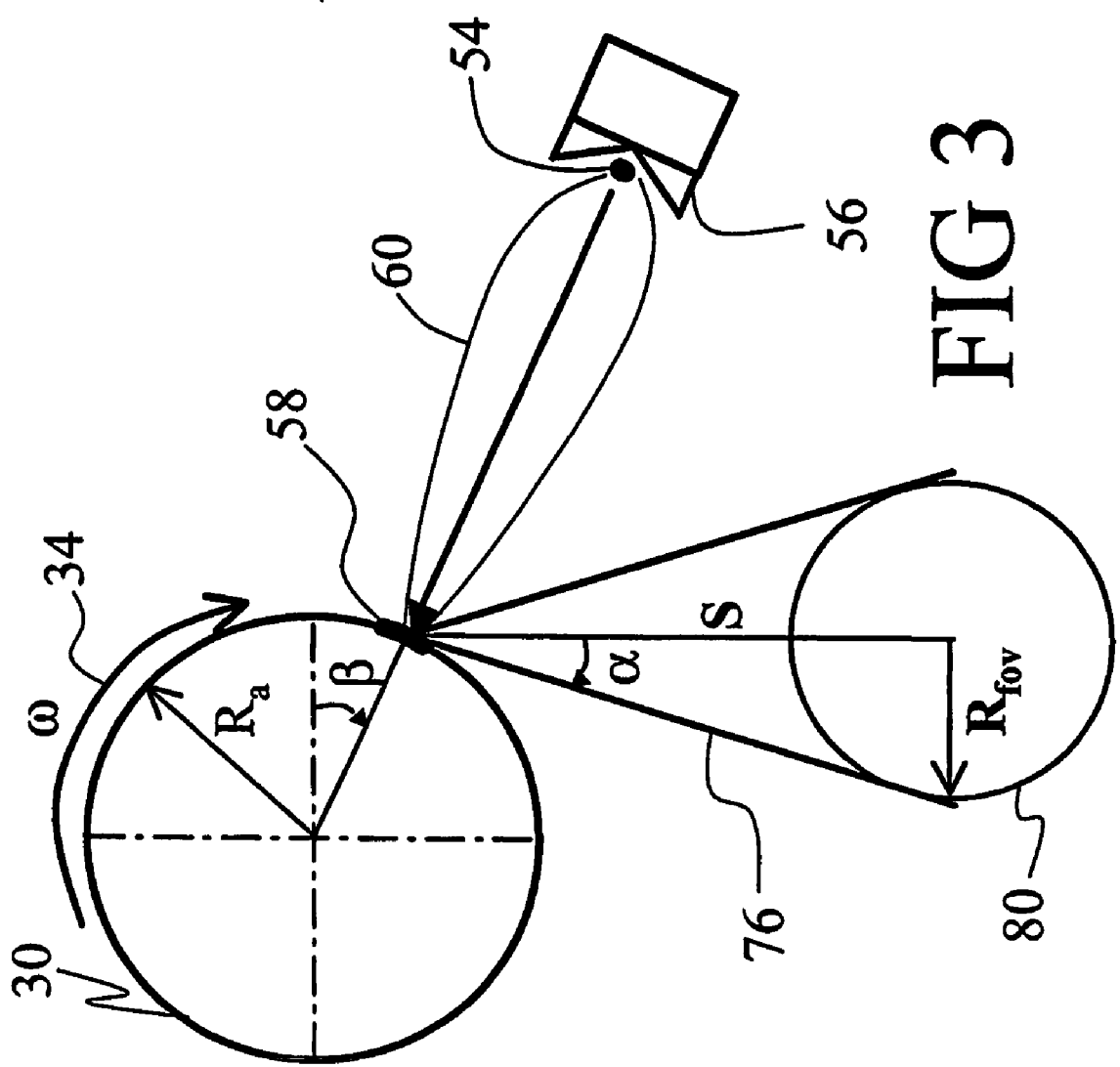

With continuing reference to FIGS. 1 and 2 and with further reference to FIG. 3, interaction of the electron beam 60 with the target outer surface region of the cylindrical anode 30 at the selected spot 58 produces an x-ray conebeam 76 emanating from the selected spot 58. The conebeam 76 diverges in the fan direction at a fan angle $\alpha$ defined by the geometry of the selected spot 58 and by a window slot 78 (see FIG. 2) formed in the evacuated frame 36 through which x-rays are emitted. The window slot 78 has a length along the longitudinal sweep trajectory 70 that is long enough to accommodate the sweep 70. The fan angle $\alpha$ is selected by a transverse width of the window slot 78 such that at a source distance S away from the x-ray source 12 the conebeam spans a spherical field of view 80 having a radius $R_{fov}$. Specifically, $R_{fov}=S\cdot\sin(\alpha)$. (Note that FIG. 3 is diagrammatic and not drawn to the preferred scale. A radius $R_a$ of the cylindrical anode 30 is preferably substantially less than the source distance S). The field of view 80 is preferably disposed in the examination region 14 and encompasses a imaging region of interest of the imaging subject.

Figure 4:
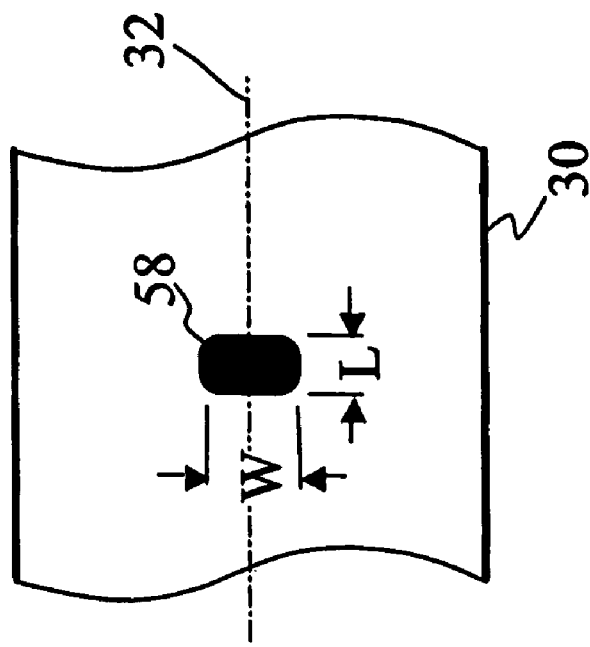

With continuing reference to FIGS. 1-3 and with further reference to FIG. 4, the selected spot 58 has dimensions of length L measured along the direction of the cylinder axis 32 and width W measured along the direction of rotation 34. In a preferred embodiment, the electron beam 60 strikes the cylindrical anode 30 substantially perpendicularly to the anode surface at sweep center, that is at about a 90° angle respective to the anode surface when the beam is at about the middle of the sweep trajectory 70, as shown in FIG. 3. Perpendicular impingement of the electron beam 60 on the cylindrical anode 30 provides a small length L of the selected spot 58, which supports a large cone angle and a long beam sweep trajectory 70. In contrast, existing disk anodes typically have an anode angle of about 15° or less, which substantially limits the cone angle due to the heel effect. In addition to providing an advantageously larger cone angle, the cylindrical anode 30 provides improved resolution uniformity due to the substantially perpendicular electron beam impingement angle on the anode surface. In contrast, the shallow anode angle used in disk anodes produces an elongated spot on the anode surface which leads to substantial anisotropic resolution uniformity.

The fan angle $\alpha$ of the conebeam 76 is related to an angle $\beta$ of the electron beam 60 relative to a direction toward the imaging subject (where at $\beta=0°$ the electron beam 60 strikes the anode perpendicularly to the direction of the source distance S) in that $\beta > \alpha$. Thus, a larger electron beam angle $\beta$ supports a larger fan angle $\alpha$. This is countered, however, by a decrease in instantaneous power as the electron beam angle $\beta$ increases. The electron beam angle $\beta$ is preferably selected as being about 3°-4° greater than the fan angle $\alpha$ to maximize power output. For an exemplary source distance S=57.5 cm and a field of view $R_{fov}$=25 cm, the fan angle $\alpha$ should be about 26°, and the electron beam angle $\beta$ is preferably about 29° to 30°. If $R_{fov}$ is reduced to 12.5 cm, the fan angle $\alpha$ should be about 13°, and the electron beam angle $\beta$ is preferably about 16° to 17°.

The reduced spot length L providing improved resolution uniformity comes at a cost in x-ray power. The maximum instantaneous x-ray power output P is related to parameters of the x-ray tube 12 according to:

$$P \propto \Delta T \cdot L \cdot \sqrt{W \cdot R_a \cdot \omega} \qquad (1)$$

where $\Delta T$ is a temperature difference between a peak temperature $T_{peak}$ at the selected spot 58 and a base background temperature $T_{base}$ of the cylindrical anode 30, and $\omega$ is a rotation speed of the cylindrical anode rotation 34. The reduced power due to reduced spot length L can be at least partially compensated in several ways. The temperature difference ΔT is increased due to a reduced base temperature $T_{base}$ of the cylindrical anode 30 that results from distributing the heating along the beam sweep trajectory 70. The electron beam angle β is preferably minimized for a given fan angle α to maximize power. The rotation speed ω of the cylindrical anode 30 can also be increased compared with a disk anode due to improved anode balance and low weight distribution of the cylindrical anode 30 which reduces wobble.

By distributing the heating along the beam sweep trajectory 70, the cylinder radius $R_a$ can be reduced compared with the diameter of a conventional disk anode. Reducing the cylinder radius $R_a$ can increase the target velocity. Although the target velocity of Equation (1) given by $R_a \cdot \omega$ is proportional to anode radius $R_a$, reducing the radius $R_a$ also reduces the moment of inertia of the cylindrical anode, which is proportional to $mR_a^2$ where m is the anode mass. For a solid cylindrical anode, the mass m is proportional to the anode volume which is given by $\pi R_a^2 h$ where h is the cylinder height. Hence, the moment of inertia of the cylindrical anode 30 is proportional to $R_a^4$, and so the reduction in target velocity due to the reduced radius $R_a$ can be overcome by a larger increase in rotational velocity ω due to the substantial decrease in moment of inertia with decreasing radius $R_a$.

Figure 5:
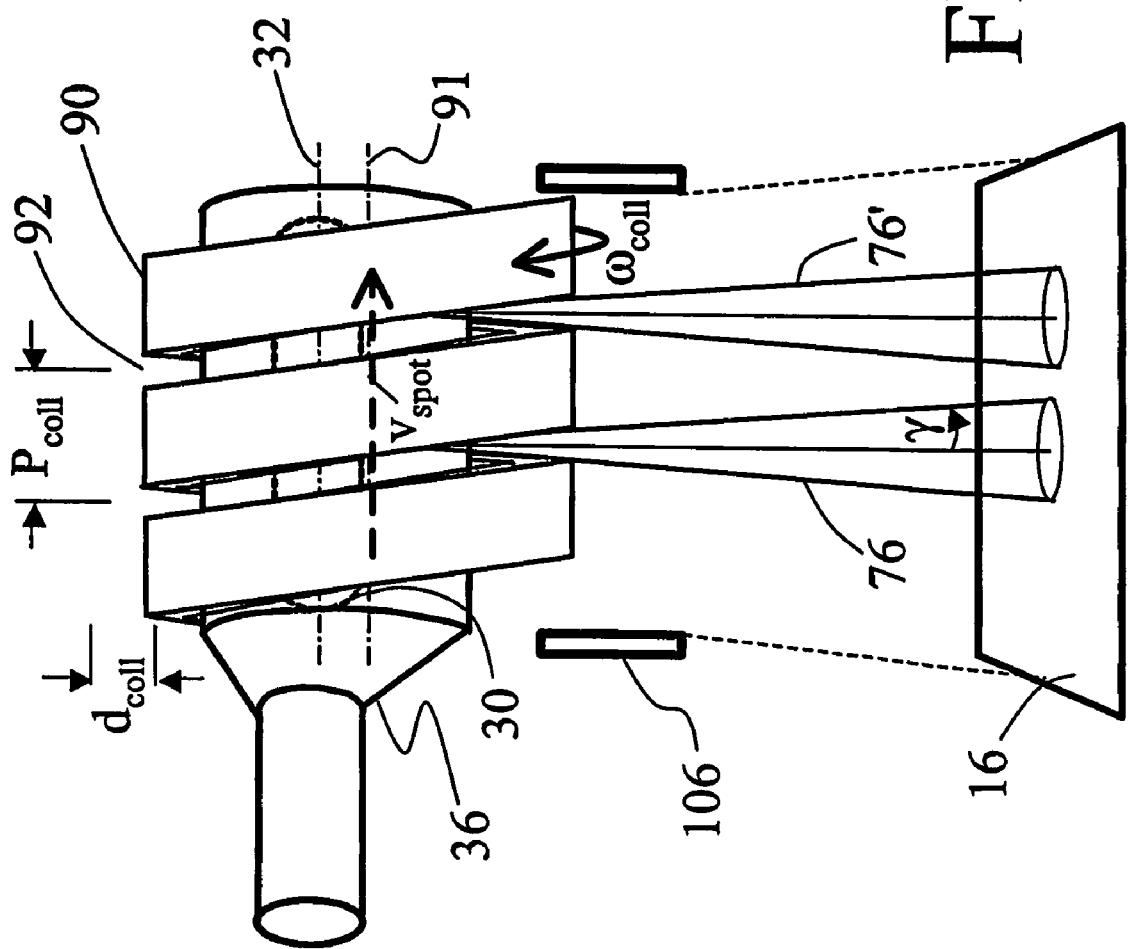
FIG. 5 shows a side view of the x-ray tube of FIG. 2 and an associated rotating helical-slot collimator.

With continuing reference to FIGS. 1-4 and with further reference to FIG. 5, a rotating cylindrical helical-slot collimator 90 provides collimation for the conebeam 76 in the cone angle direction. The collimator 90 is generally cylindrical and generally hollow, and surrounds the evacuated frame 36 of the x-ray tube 12. The cylinder form of the cylindrical collimator 90 has a collimator cylinder axis 91 that is parallel to the cylinder axis 32 of the cylindrical anode 30, and rotates about the cylinder axis 32 at a rotation speed $\omega_{coll}$. Preferably, the collimator cylinder axis 91 corresponds to the spot trajectory $v_{spot}$ as shown in FIG. 5 for convenience and accuracy in aligning the x-ray generating spot with the collimator 90. However, the collimator cylinder axis 91 optionally deviates from the spot trajectory $v_{spot}$ to accommodate space constraints or mechanical considerations.

To accommodate the sweep 70, the rotating helical-slot collimator 90 has a helical slot 92 of pitch $P_{coll}$ as indicated in FIG. 5. The rotation speed $\omega_{coll}$ is selected such that a continuously shifting portion of the helical slot 92 crossing the helical sweep trajectory 70 moves at a velocity $P_{coll} \cdot \omega_{coll}$ where the collimator slot pitch $P_{colls}$ and the collimator rotation speed $\omega_{coll}$ are selected to match a sweep speed $v_{spot}$ of the x-ray generating spot 58. That is, $v_{spot} = P_{coll} \cdot \omega_{coll}$ where $\omega_{coll}$ is measured in units of number of rotations per unit time. It will be appreciated that the rotation speed $\omega_{coll}$ of the collimator 90 is independent of and generally different from the rotation speed ω of the cylindrical anode 30. Moreover, the anode and collimator rotations can be in the same direction or in opposite directions, depending upon the handedness of the helical slot 92.

Figure 6:
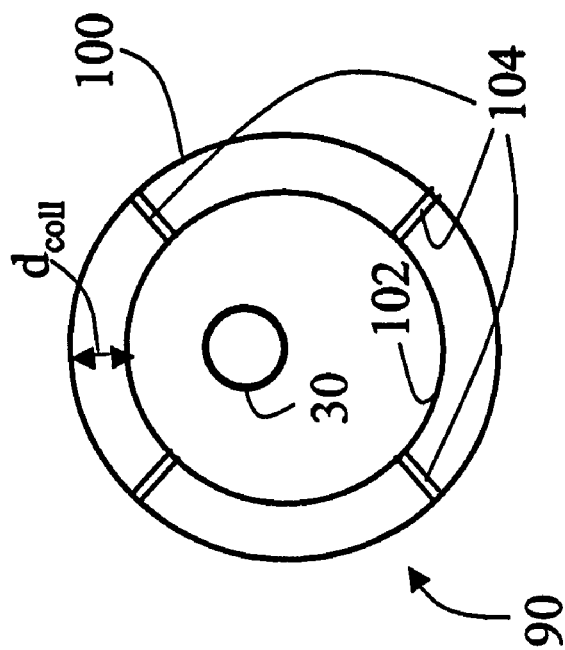
FIG. 6 shows an end view of a preferred tube-within-a-tube construction of the rotating helical-slot collimator.

With continuing reference to FIG. 5 and with further reference to FIG. 6, a width of the helical slot 92 and radius of the collimator 90 is selected to provide a selected cone angle γ. The helical slot 92 should have a suitable depth in the direction of emission of the conebeam 76 to provide the collimation. In a preferred embodiment described with reference to FIG. 6, the collimator 90 includes an outer cylindrical shell 100 having an outer edge of the helical slot 92 defined therein, and an inner cylindrical shell 102 having an inner edge of the helical slot 92 defined therein. The outer and inner cylindrical shells 100, 102 are secured together in a spaced-apart arrangement by spacer elements 104 with the outer and inner helix edges of the shells 100, 102 aligned to define the helical slot 92.

In another embodiment, the spacer elements 104 can be replaced by a single continuous helical spacer element having a pitch equal to that of the slot 92. With such a helical spacer element, the cylindrical shells 100, 102 can be threaded or screwed onto the helical spacer element. In yet another embodiment, the spacer elements 104 are replaced by a solid cylindrical shell of thickness $d_{coll}$ made of a material that is substantially transparent to the x-rays. For example, a rigid foam cylindrical support shell can be used. Moreover, the two cylindrical shells 100, 102 can be replaced by a single-piece hollow cylindrical shell with the helical slot formed therein that has a substantial annular thickness that provides the selected collimating depth $d_{coll}$ in the direction of emission of the conebeam 76.

Advantageously, the rotating cylindrical helical-slot collimator 90 can support simultaneous collimation of a plurality of axially spaced x-ray beams. As shown in FIG. 5, a second x-ray conebeam 76' is axially spaced from the conebeam 76 by the pitch $P_{coll}$ of the helical slot 92. Generation of the second conebeam 76' is effected by a second filament and cathode cup (not shown) corresponding to the filament 54 and cathode cup 56 (see FIG. 2) that accelerate and focus electrons generated by the second filament toward a second selected focal spot on a target outer surface region of the cylindrical anode 30 that is axially spaced from the focal spot 58 generated by the filament/cup 54, 56 by about the pitch $P_{coll}$.

Similarly, three or more conebeams spaced by the collimator slot pitch $P_{coll}$ can be supported by including suitable corresponding filament/cathode cup generating elements. The number of x-ray beams that can be so supported is limited by geometrical constraints such as the axial extent of the anode 30, the pitch $P_{coll}$, and the axial spread of the beams at the x-ray detector 16. The latter constraint is geometrically related to the cone angle γ of the beams and the source-to-detector distance. Axial sweeping of the plurality of beams can be accomplished using the electrodes 64, 68 of the electrostatic beam deflector (see FIG. 2). Alternatively, a separate, dedicated beam deflector can be provided for each x-ray beam with the plurality of beam deflectors temporally synchronized to coordinate the sweeping.

The outer and inner cylindrical shells 100, 102 provide the collimation depth $d_{coll}$ that together with the selected collimator radius ensures that x-rays from the multiple x-ray generating spots are each collimated by a single turn of the helical slot 92, so that for example the portion of the helical slot 92 that collimates the conebeam 76 does not also allow x-rays generated by the x-ray generating spot corresponding to the conebeam 76' to pass. Moreover, a fixed axially-limiting collimator 106 is preferably provided to provide a relatively sharp and fixed cutoff (indicated by dashed lines in FIG. 5) of the sweeping x-ray beams 76, 76' as they reach axial edges of the x-ray detector 16.

With returning reference to FIG. 1, projection data acquired by the x-ray source 12 (which includes the cylindrical anode 30, sweeping x-ray spot 58, cylindrical collimator 90, and so forth as already described with reference to FIGS. 2-6) is stored in an acquired data memory 110. In conventional computed tomography using a substantially fixed x-ray beam focal spot (neglecting an optional focal spot wobble or other de minimus movement of the focal spot), the spatial orientation of the projections are fully defined based on the position of the x-ray source 12 and the array element of the x-ray detector 16 used to acquire the projection. In the x-ray computed tomography scanner 10, however, the projection orientation also depends upon the position of the focal spot 58 along the sweep trajectory 70.

An anode sweep correction processor 112 receives a sweep position signal from a beam sweep controller 114 and makes suitable longitudinal position and axial angular orientations adjustments of the acquired projections to account for the axial position of the x-ray beam or beams. The corrected projection data is input to a reconstruction processor 120 that performs image reconstruction by applying three-dimensional filtered backprojection or another suitable reconstruction algorithm. The resulting reconstructed image is stored in an image memory 122, processed by a video processor 124, and displayed to a radiologist or other operator on a video monitor of a user interface 126, for example, as a slice, plurality of slices, a three-dimensional rendering, or other suitable human-viewable representation. The reconstructed image can also be printed by a graphical printer, stored in a database, transmitted over a local area network or the Internet, or otherwise processed.

Preferably, the user interface 126 also enables the radiologist or other operator to communicate with a computed tomography controller 130 to control the computed tomography scanner 10. It will be appreciated that axial movement of the conebeam relative to an imaging subject disposed on the subject support 20 can be accomplished in three ways: (i) the beam sweep 70 can be used to sweep the conebeam while the subject support 20 (and hence the imaging subject) remains stationary; (ii) a combination of the beam sweep 70 and linear movement of the imaging subject via the subject support 20 can be employed; or (iii) the subject support 20 can move the subject linearly in the axial direction while the beam sweep 70 across the cylindrical anode is turned off.

In approach (i), longitudinal scanning is accomplished solely through sweeping of the selected spot 58. Hence, the beam sweep trajectory 70 should span the imaging volume. In cardiac imaging, for example, a longitudinal scan of about 12 cm is typically desired, and so the beam sweep trajectory 70 should span at least 12 cm. Moreover, the longitudinal beam sweep should be coordinated with angular rotation of the gantry 22 to ensure sufficient angular coverage for each voxel in the imaged volume. Preferably, a synchronization circuit 132 receives the rotating gantry angular position as an input, and outputs a synchronization signal to the beam sweep controller 114 to coordinate the revolving of the x-ray source 12 and the longitudinal scanning in the data acquisition.

In approach (ii), longitudinal scanning is accomplished by a combination of longitudinal beam sweep and longitudinal motion of the subject support 20. In this case, the beam sweep trajectory 70 can be less than the longitudinal length of the imaging volume. In one contemplated variation, the sweep trajectory 70 is relatively small, the beam sweep speed $v_{spot}$ is substantially higher than the longitudinal motion of the subject support 20, and the beam sweep is not relied upon to provide longitudinal data acquisition coverage, but rather only to provide heat distribution across the cylindrical anode 30. In this variation, the synchronization circuit 132 does not synchronize the beam sweep with gantry rotation. In other contemplated variations, the beam sweep trajectory 70 contributes to the longitudinal component of the scanning and is coordinated by the synchronization circuit 132 with the gantry rotation to provide selected angular coverage characteristics in the data acquisition. U.S. patent application Ser. No. 10/280,734 by Heuscher, filed Oct. 25, 2002, describes suitable longitudinal sweep/gantry rotation synchronization schemes for obtaining optimized temporal and/or spatial resolution using approaches (i) and (ii). In another variation, the beam sweep and the support movement are the same such that the beam remains stationary relative to the subject while still distributing heat across the anode.

The third approach (iii) in which the beam sweep 70 is turned off operates as a conventional computed tomography system having a fixed axial position of the x-ray source relative to the x-ray detector. In approach (iii), the anode sweep correction processor 112 is obviated. A substantial thermal disadvantage arises with approach (iii), however, because without sweeping the x-ray generating spot 58 follows a rapidly repeating circular path around the cylindrical anode 30. Most of the surface of the cylindrical anode 30 is unused, and so heat is not distributed across the cylindrical anode.

Figure 7:
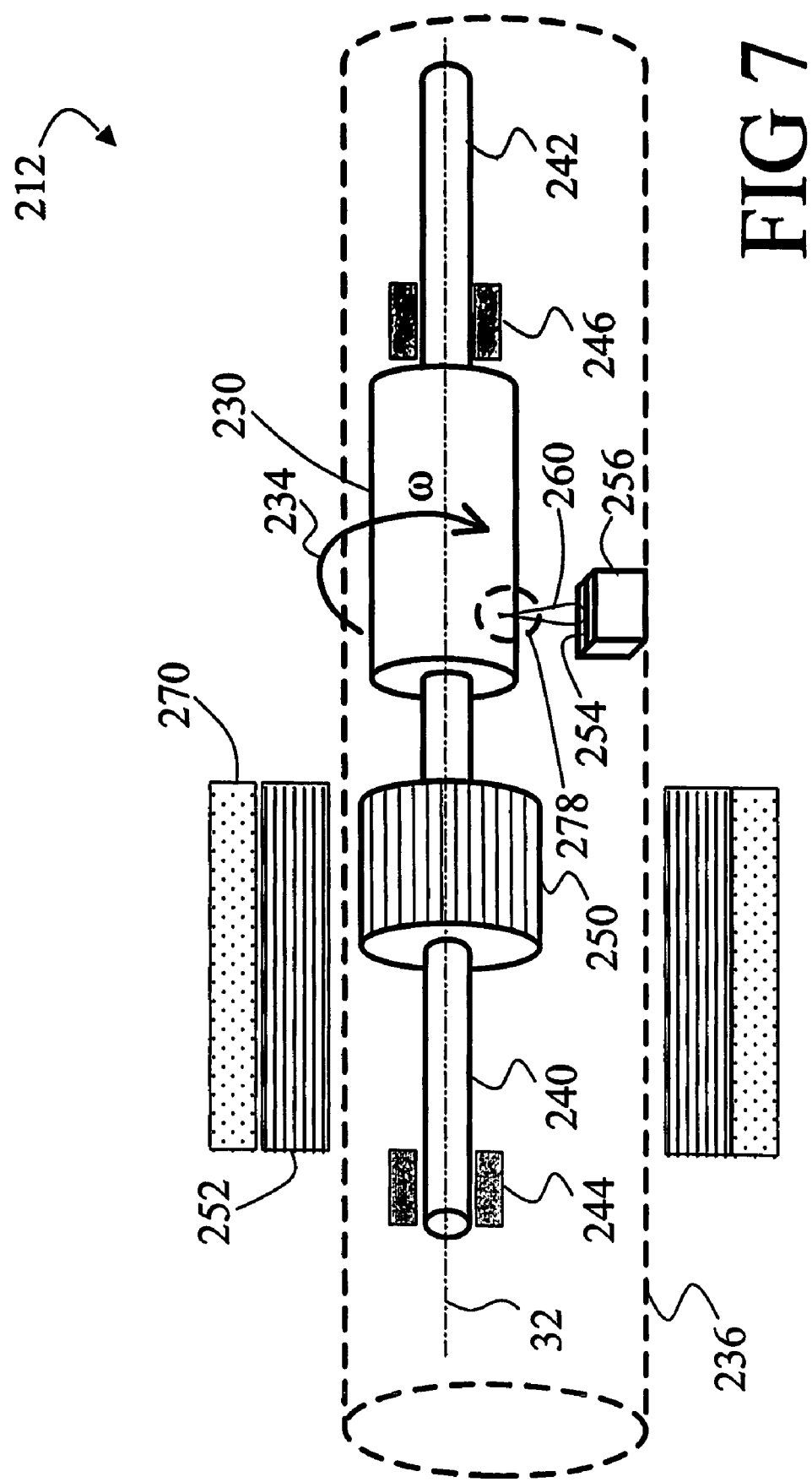
FIG. 7 shows a second embodiment of the x-ray tube, in which the cylindrical anode is reciprocated back-and-forth.
Figure 8:
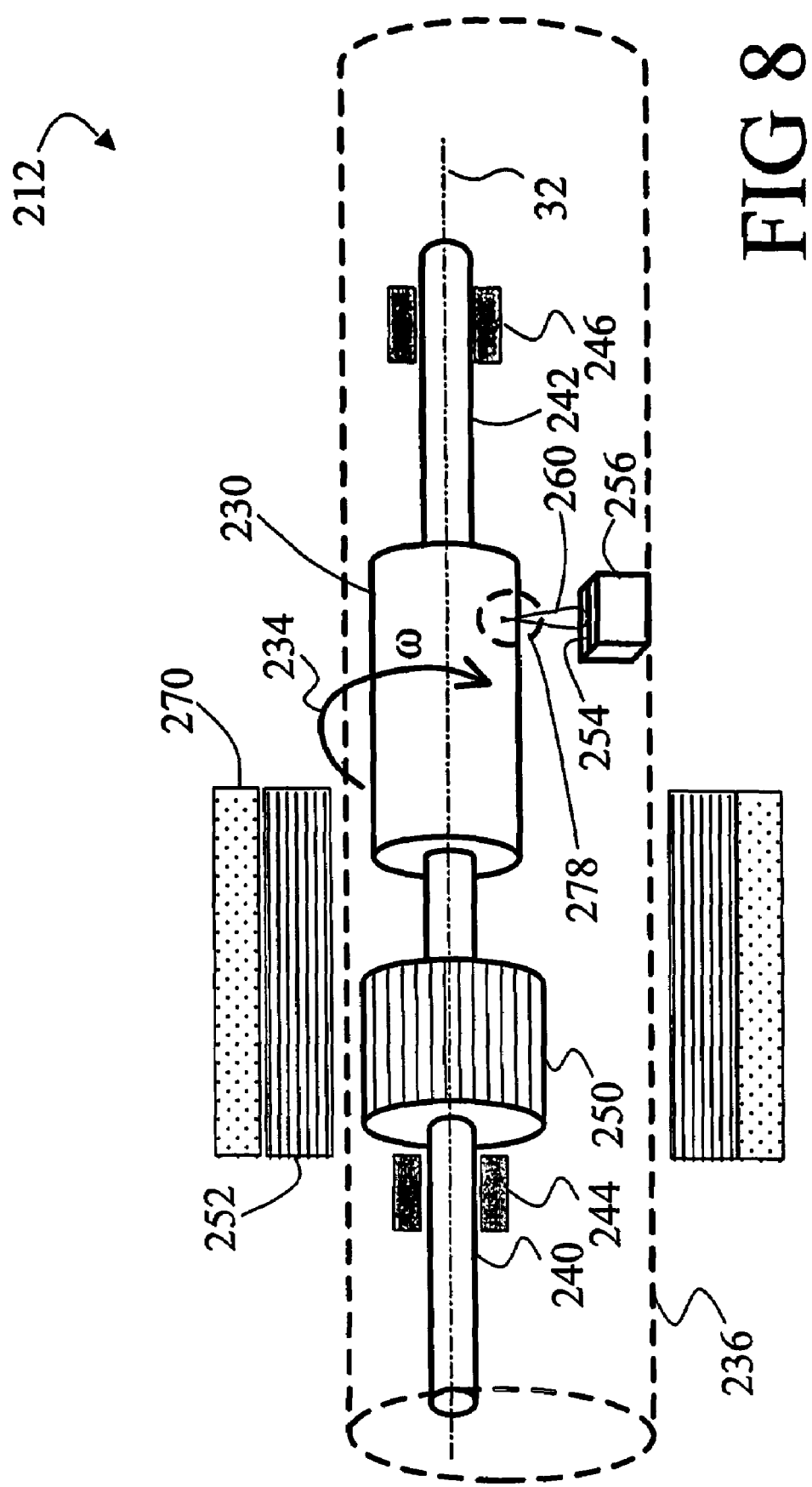
FIG. 8 shows the x-ray tube of FIG. 7 with the reciprocating anode at an opposite end of the reciprocation cycle.

With reference to FIGS. 7 and 8, a modified x-ray tube 212 that suitably replaces the x-ray tube 12 has a longitudinally reciprocating rotating cylindrical anode 230. FIGS. 7 and 8 show the x-ray tube 212 with a cylindrical anode 230 at opposite limits of a back-and-forth reciprocating. The cylindrical anode 230 also rotates about the cylinder axis 32 at anode rotation speed ω as indicated by a curved rotation arrow 234. The reciprocating cylindrical anode 230 is rotatably secured within an evacuated frame 236 (shown in phantom) by a drive shaft 240 and an end shaft 242, which in turn are supported by bearing assemblies 244, 246, such as magnetic bearings, that are secured to the evacuated frame 236. The shafts 240, 242 are longer than corresponding shafts 40, 42 of the x-ray tube 12, in order to accommodate longitudinal anode reciprocation. Moreover, the bearing assemblies 244, 246 should be selected to support sliding longitudinal shaft motion as well as shaft rotation. Motor rotor windings 250 disposed on the drive shaft 240 cooperate with stationary motor stator windings 252 (shown by sectional portion) disposed outside the evacuated frame 236 to effect rotation of the cylindrical anode 230.

A filament 254 and a cathode cup 256 (which are similar in operation to the filament 54 and cup 56 of the x-ray tube 12) generate an electron beam 260 that strikes the cylindrical anode 230 to define an x-ray generating spot. Unlike the x-ray tube 12, there is no beam deflector for sweeping the electron beam longitudinally across the anode 230. Rather, to provide heat distribution across the anode without shifting the focal spot, the anode 230 reciprocates relative to the electron beam 260. Reciprocation of the anode 230 is suitably effected using one or more solenoid windings 270 disposed outside the evacuated frame 236 that produce magnetic fields interacting with the motor rotor windings 250 and/or the drive shaft 240 to effect longitudinal motion of the drive shaft 240 and the attached cylindrical anode 230 and end shaft 242. It will be noted that both the motor stator windings 252 and the solenoid windings 270 extend over a longitudinal distance substantially corresponding to the distance of anode reciprocation. In other words, the motor rotor windings 250 remain inside the motor stator windings throughout the reciprocating. The x-ray tube 212 does not have a sweeping focal spot, and so there is no cylindrical collimator. Rather, an x-ray emission window 278 is formed into the evacuated frame 236 and provides collimation in both the fan and cone angle directions. Alternatively or in addition, an external pinhole, slat, or other collimator can be arranged outside the evacuated frame 236 to provide collimation.

Back-and-forth reciprocation of the cylindrical anode 230 provides heat distribution across the anode surface. This motion is independent of any longitudinal motion of helical scanning, and is preferably optimized to provide uniform heat distribution With reference to FIG. 9, one suitable anode reciprocation trajectory 290 is shown as a plot of anode position versus time. The maximum anode position 292 corresponds to the configuration shown in FIG. 7, while the minimum anode position 294 corresponds to the configuration shown in FIG. 8. The trajectory 290 is a superposition of a low amplitude first oscillation at a high frequency $f_1$ on a higher amplitude second oscillation at a lower frequency $f_2$. The trajectory 290 distributes hot spots at the ends of each low amplitude $f_1$ oscillation (that is, where the velocity crosses zero) longitudinally across the anode. The anode rotation speed $\omega$ and longitudinal oscillation frequencies $f_1$, $f_2$ are preferably selected to distribute the hot spots around the circumference of the anode 230. (For example, if $\omega$ is a multiple of $f_1$, then successive hot spots will occur at about the same angle of rotation of the anode 230, which disadvantageously concentrates heating on one side of the anode 230). The trajectory 290 is exemplary only; those skilled in the art can readily compute a suitable trajectory for specific anode rotation speeds, anode axial reciprocation rates, and thermal characteristics of the anode.

Although only a single filament 254 and cathode cup 256 are shown in FIGS. 7 and 8, it will be appreciated that a plurality of filament 254/cup 256 sources can be arranged in axially spaced fashion along the cylindrical anode 230 to produce a corresponding plurality of axially spaced apart x-ray generating spots. In this manner, a plurality of fixed-position axially spaced apart x-ray beams can be generated by the cylindrical anode 230. The anode length and the axial extent of the longitudinal anode reciprocation is preferably selected to ensure that the x-ray generating spots remain on the cylindrical anode throughout the longitudinal reciprocation cycle.

To mechanically balance the axial reciprocating motion of the anode 230 on the rotating gantry 22, one or more reciprocating counterweights (not shown) are optionally provided. In one contemplated balancing configuration, two reciprocating counterweights are arranged on opposite sides of the x-ray tube 212, with each counterweight having one-half of the combined mass of the reciprocating anode 230 and shafts 240, 242 and having axial reciprocating motion in opposition to the reciprocating motion of the anode 230.

The cylindrical anodes 30, 230 are shown as solid cylinders which are preferably made of a high x-ray yield material, that is, a material that produces a high x-ray yield responsive to irradiation by electrons of the electron beam 60, 260. Moreover, the material should be a refractory metal or other material capable of withstanding the instantaneous peak temperature $T_{peak}$ at the point where the x-rays are being generated as well as the elevated base background temperature $T_{base}$ of the cylindrical anode during operation. The drive shaft 40, 240 and end shaft 42, 242 are secured to the anode 30, 230. Alternatively, the drive shaft 40, 240 and end shaft 42, 242 form a single unitary shaft, and the anode 30, 230 has a hollow center through which the single unitary shaft passes. A disadvantage of the solid anode 30, 230 is that the high x-ray yield material may be non-optimal in terms of density or thermal conductivity. For example, tungsten is relatively dense, which increases the moment of inertia of the cylindrical anode 30, 230, making high speed anode rotation more difficult.

With reference to FIG. 10, an anode 330 is suitably substituted for either the non-reciprocating anode 30 or the reciprocating anode 230. The anode 330 is secured to drive shaft 340 and end shaft 342, which are optionally a single unitary shaft passing through the anode 330. The anode 330 includes a lightweight central supporting cylinder 350 made of aluminum, copper, brass, alloys thereof, or another lightweight, thermally conductive material, and a metallic coating or sleeve 352 made of tungsten or another material selected for high electron yield and good thermal stability.

With reference to FIG. 11, another anode 430 is suitably substituted for either the non-reciprocating anode 30 or the reciprocating anode 230. The anode 430 is secured to a unitary shaft 440 that provides both drive shaft and end shaft functions. The anode 430 includes an outer hollow cylindrical shell 450 made of tungsten or another material selected for high electron yield and good thermal stability. Optionally, the hollow cylindrical shell is made of a lightweight material covered by a coating of a high x-ray yield material such as tungsten. One or more structural support members, specifically nine structural support members 452 shown in phantom in FIG. 11, mechanically secure the outer hollow cylindrical shell 450 to the unitary shaft 440.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having described the preferred embodiments, the invention is now claimed to be:

1. An x-ray tube that injects an x-ray conebeam into an examination region, the x-ray tube including:
    a rotating cylindrical anode having a target outer surface region, the cylindrical anode rotating about a longitudinally aligned cylinder axis;
    a rotating helical-slot collimator that rotates around the cylindrical anode;
    an electron accelerating means for accelerating electrons toward at least one selected spot on the target outer surface region of the cylindrical anode to generate x-rays; and
    a sweep means for relatively longitudinally sweeping the at least one selected spot across the target outer surface region of the cylindrical anode in coordination with rotating the helical-slot collimator.

2. The x-ray tube as set forth in claim 1, wherein the cylindrical anode includes:
    a central supporting cylinder; and
    a metallic layer at least a portion of which defines the target outer surface region.

3. The x-ray tube as set forth in claim 2, wherein the central supporting cylinder includes:
    an outer shell defining a hollow cylinder core; and
    at least one structural support member disposed in the hollow cylinder core, the at least one structural support member mechanically coupled to an associated rotating shaft.

4. The x-ray tube as set forth in claim 2, wherein the metallic layer is a tungsten coating.

5. The x-ray tube as set forth in claim 1, wherein the cylindrical anode includes:
    a substantially solid metallic cylinder, at least a portion of an outer surface of said solid metallic cylinder defining the target outer surface region of the cylindrical anode.

6. The x-ray tube as set forth in claim 1, wherein the cylindrical anode includes:
a substantially hollow outer cylindrical shell; and
at least one structural support member disposed in the substantially hollow outer cylindrical shell, the at least one structural support member mechanically coupled to an associated rotating shaft.

7. The x-ray tube as set forth in claim 1, wherein the accelerated electrons define an electron beam, and the sweep means includes:
an electron deflector that selectively deflects the electron beam to sweep the at least one selected spot across the target outer surface region of the cylindrical anode.

8. The x-ray tube as set forth in claim 7, wherein the helical-slot collimator has a helical collimating slot formed therein, surrounds the rotating cylindrical anode, and rotates about a collimator axis parallel to the cylinder axis, and a helical pitch of the helical collimating slot and a rotation rate of the collimator, relative to the sweep of the at least one selected spot, are such that the at least one selected spot coincides with the helical-slot during the sweeping.

9. The x-ray tube as set forth in claim 8, further including:
an evacuated frame that surrounds the rotating cylindrical anode, the rotating cylindrical helical-slot collimator being arranged outside of the evacuated frame.

10. The x-ray tube as set forth in claim 8, wherein the rotating cylindrical helical-slot collimator includes:
an outer cylindrical shell surrounding the rotating cylindrical anode and aligned with the collimator axis, the outer cylindrical shell having a first helical slot defined therein; and
an inner cylindrical shell surrounding the rotating cylindrical anode and disposed inside the outer cylindrical shell, the inner cylindrical shell being aligned with the collimator axis and having a second helical slot defined therein that aligns with the first helical slot, the first and second helical slots cooperatively defining the helical collimating slot.

11. The x-ray tube as set forth in claim 10, wherein the outer and inner cylindrical shells are secured together and rotate as a unit.

12. The x-ray tube as set forth in claim 8, further including:
a fixed axially limiting collimator that axially limits the x-rays.

13. The x-ray tube as set forth in claim 1, wherein the sweep means includes:
a longitudinal reciprocating mechanism longitudinally reciprocating the cylindrical anode to effect a longitudinal reciprocating sweep of the at least one selected spot across the target outer surface region of the cylindrical anode.

14. A CT scanner including:
a rotating gantry which rotates around an examination region and an axis of revolution;
an x-ray tube being mounted to the rotating gantry with a cylinder axis parallel to the axis of revolution, wherein the x-ray tube includes:
a rotating cylindrical anode having a target outer surface region, the cylindrical anode adapted to rotate about a longitudinally aligned cylinder axis;
an electron accelerator adapted to accelerate a beam of electrons toward at least one selected spot on the target outer surface region of the cylindrical anode to generate x-rays;
a focal spot positioning component for relatively longitudinally sweeping the at least one selected spot across the target outer surface region of the cylindrical anode; and
a rotating cylindrical helical-slot collimator, surrounding the rotating cylindrical anode, adapted to collimate the generated x-rays as the spot sweeps across the target;
an x-ray detector arranged to detect x-rays after the x-rays pass through the examination region; and
a reconstruction processor for reconstructing output signals from the x-ray detector into an image representation.

15. The CT scanner as set forth in claim 14, further including:
a synchronization circuit that synchronizes the sweep with rotation of the rotating gantry.

16. The CT scanner as set forth in claim 14, wherein the cylindrical helical-slot collimator has a helical collimating slot formed therein and rotates about a collimator axis that is parallel to the cylinder axis, a helical pitch of the helical collimating slot and a rotation rate of the collimator being selected relative to the sweep of the at least one selected spot such that the at least one selected spot coincides with the helical-slot during the sweeping.

17. A method of generating x-rays including:
rotating a cylindrical anode about a cylinder axis, the cylindrical anode having a cylindrical target outer surface region;
rotating a helical-slot collimator around a collimator axis that is parallel to the cylinder axis;
accelerating electrons toward at least one selected spot on the target outer surface region of the cylindrical anode to generate x-rays; and
relatively sweeping the at least one selected spot continuously across the target outer surface region of the cylindrical anode along a beam trajectory substantially parallel to the cylinder axis and in coordination with rotating the helical-slot collimator.

18. The method as set forth in claim 17, wherein the relative sweeping includes:
steering at least one electron beam defined by the accelerated electrons longitudinally across the cylindrical anode.

19. The method as set forth in claim 18, wherein the relative sweeping includes:
fast-retracing the at least one electron beam to return to a longitudinal sweep starting point subsequent after each longitudinal sweep across the cylindrical anode.

20. The method as set forth in claim 17, wherein the relative sweeping includes:
longitudinally reciprocating the cylindrical anode to effect longitudinal reciprocating sweeping of the at least one selected spot on the target outer surface region of the cylindrical anode.

21. The method as set forth in claim 17 wherein the collimator axis corresponds to the beam trajectory.

22. The method as set forth in claim 17 wherein the at least one selected spot includes a plurality of spots separated by a helical pitch of a helical slot of the helical-slot collimator that generate a corresponding plurality of x-ray beams.

23. The method as set forth in claim 17, further including:
rotating the cylindrical anode around an axis of rotation, the axis of rotation being parallel to the cylindrical axis;

sweeping the at least one selected spot in coordination with the rotating;

detecting the x-rays which have passed through a subject along the axis of rotation;

converting the detected x-rays into an image of the subject.

24. An x-ray tube, comprising:

a rotating cylindrical anode;

an electron accelerator that accelerates electrons toward a region on the surface of the cylindrical anode to produce a focal spot;

an anode positioner that selectively positions the cylindrical anode longitudinally with respect to the electron accelerator, and a rotating cylindrical helical-slot collimator adapted to collimate a radiation beam emitted from the focal spot.

25. The x-ray tube of claim 24, wherein the anode positioner reciprocates the cylindrical anode to sweep the accelerated electrons back and forth along the anode and, thereby, sweep the focal spot back and forth along the anode.

26. The x-ray tube of claim 24, wherein the cylindrical helical-slot collimator surrounds the cylindrical anode and rotates about a collimator axis that is parallel to a cylinder axis.

27. The radiation source x-ray tube of claim 24, wherein the x-ray tube is part of a computed tomography system.

* * * * *